(12) United States Patent
Nakazawa et al.

(10) Patent No.: US 11,092,697 B2
(45) Date of Patent: Aug. 17, 2021

(54) RADIATION DETECTION DEVICE AND NUCLEAR MEDICINE DIAGNOSIS APPARATUS INCLUDING THE SAME

(71) Applicant: Shimadzu Corporation, Kyoto (JP)

(72) Inventors: Masayuki Nakazawa, Kyoto (JP); Tetsuo Furumiya, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/616,787

(22) PCT Filed: Jul. 3, 2017

(86) PCT No.: PCT/JP2017/024392
§ 371 (c)(1),
(2) Date: Nov. 25, 2019

(87) PCT Pub. No.: WO2019/008645
PCT Pub. Date: Jan. 10, 2019

(65) Prior Publication Data
US 2020/0333476 A1     Oct. 22, 2020

(51) Int. Cl.
*G01T 1/16* (2006.01)
*G01T 1/164* (2006.01)
(Continued)

(52) U.S. Cl.
CPC ........... *G01T 1/1647* (2013.01); *A61B 6/037* (2013.01); *G01T 1/247* (2013.01); *G01T 1/249* (2013.01)

(58) Field of Classification Search
CPC ....... G01T 1/1647; G01T 1/247; G01T 1/249; A61B 6/037
See application file for complete search history.

(56) References Cited

U.S. PATENT DOCUMENTS

2003/0080298 A1*  5/2003  Karplus ................. G01T 1/247
                                                              250/370.1
2006/0192128 A1*  8/2006  Benlloch Bavciera .....................
                                                              G01T 1/1642
                                                              250/369

(Continued)

FOREIGN PATENT DOCUMENTS

JP     2014-160066 A     9/2014

OTHER PUBLICATIONS

Written Opinion of the International Searching Authority for PCT application No. PCT/JP2017/024392 (Form Pct/Isa/237), dated Sep. 12, 2017.

(Continued)

*Primary Examiner* — Hugh Maupin
(74) *Attorney, Agent, or Firm* — Muir Patent Law, PLLC

(57) ABSTRACT

A radiation detection device (300) is used in a nuclear medicine diagnosis apparatus, and includes a plurality of scintillators (44), a semiconductor light-receiving device (SiPM), a position detection circuit (214), and a timing detection circuit (216). Each of the scintillators converts a gamma ray emitted from a subject (15) into fluorescence. The semiconductor light-receiving device is provided corresponding to each of the scintillators and converts the fluorescence converted by a corresponding one of the scintillators into an electrical signal. The position detection circuit specifies a gamma ray detection position in the scintillators based on the electrical signal from the semiconductor light-receiving device. The timing detection circuit is connected to an anode of the semiconductor light-receiving device, and specifies time information corresponding to a time of occurrence of an event in which the gamma ray is detected.

5 Claims, 10 Drawing Sheets

(51) Int. Cl.
*A61B 6/03* (2006.01)
*G01T 1/24* (2006.01)

(56) References Cited

U.S. PATENT DOCUMENTS

| | | | |
|---|---|---|---|
| 2010/0270462 A1* | 10/2010 | Nelson | G01T 1/202 |
| | | | 250/252.1 |
| 2014/0224963 A1 | 8/2014 | Guo et al. | |
| 2015/0285922 A1* | 10/2015 | Mintzer | A61B 6/4241 |
| | | | 600/411 |

OTHER PUBLICATIONS

Bieniosek et al., "Achieving fast timing performance with multiplexed SiPMs," Physics in Medicine and Biology, vol. 61, pp. 2879 to 2892, Apr. 2016, published by Institute of Physics and Engineering in Medicine.
Notice of Reasons for Refusal for Japanese patent application. No. 2019-528212 dated Jul. 29, 2020.

* cited by examiner

RADIATION DETECTION DEVICE AND NUCLEAR MEDICINE DIAGNOSIS APPARATUS INCLUDING THE SAME

TECHNICAL FIELD

The present invention relates to a radiation detection device for detecting radiation emitted from a subject that receives administration of a radioactive medicine, and a nuclear medicine diagnosis apparatus including the radiation detection device, and more particularly to a technique for improving the accuracy of detection time and detection position for a gamma ray detected in the radiation detection device.

BACKGROUND ART

As a nuclear medicine diagnosis apparatus obtaining medical data of a subject based on radiation emitted from the subject that receives administration of a radioactive medicine, a nuclear medicine imaging apparatus such as a positron emission tomography (PET) apparatus and a single photon emission computed tomography (SPECT) apparatus is known.

By a plurality of detectors, the PET apparatus detects two gamma rays generated by positron annihilation. Specifically, a radioactive medicine (radioactive tracer) containing positron-emitting radionuclides is administered to a subject. Then, a pair annihilation gamma ray emitted from the inside of the subject that receives administration is detected by a large number of radiation detectors. Then, when a gamma ray is detected by two radiation detectors in a prescribed time period, the detected gamma ray is counted as a pair of the pair annihilation gamma rays, to specify the position of occurrence of the pair annihilation gamma ray on a straight line connecting two detection positions where radiation is detected. In a time-of-flight (TOF)-type PET apparatus, the difference in detection time between the pair of the pair annihilation gamma rays detected by two detectors is utilized to specify the point at which the pair annihilation gamma ray occurs on the above-mentioned straight line. Then, the dose distribution of the detected gamma rays is imaged, so that a nuclear medicine image can be obtained.

A detector used for detecting a gamma ray in a nuclear medicine diagnosis apparatus like a PET apparatus generally includes: a scintillator that receives a gamma ray and converts the received gamma ray into fluorescence exhibiting a peak in an ultraviolet range; and a light-receiving device that multiplies a photoelectron from the scintillator and converts the multiplied photoelectron into an electrical signal As a light-receiving device, a photomultiplier tube (PMT) formed using a plurality of dynodes have conventionally been adopted. However, in recent years, there is also a light-receiving device formed using a silicon photomultiplier (SiPM) including an avalanche photodiode (APD) as a semiconductor device array. Since the SiPM has a property that is less likely to be influenced by magnetism as compared with a PMT, it can be applied also to an apparatus constituted of a magnetic resonance imaging (MRI) device and a nuclear medicine diagnosis apparatus that are integrated with each other.

In the present specification, a device that converts a gamma ray into an electrical signal will be referred to as a "radiation detector (or a gamma ray detector)", and the configuration including the radiation detector and a signal processing circuit in a stage subsequent thereto will be referred to as a "radiation detection device".

CITATION LIST

Non Patent Literature

NPL 1: "Achieving fast timing performance with multiplexed SiPMs" by M. F. Bieniosek, J. W. Cates, and C. S. Levin (Institute of Physics and Engineering in Medicine; Physics in Medicine and Biology, Vol. 61, pages 2879 to 2892, April 2016)

SUMMARY OF INVENTION

Technical Problem

A nuclear medicine diagnosis apparatus requires an image with a higher resolution. In order to satisfy this requirement, a radiation detector including a plurality of light-receiving devices disposed in an array pattern may be used. Such a configuration allows more accurate detection of the position at which a gamma ray is incident in a detectable region of the radiation detector.

In order to improve the position detection accuracy of the radiation detector in such a configuration, it is more preferable to provide an individual read circuit in each of the plurality of light-receiving devices. However, when a large number of light-receiving devices (for example, 100×100) are disposed in a two-dimensional array pattern in one radiation detector, several thousands to several tens of thousands of read circuits are required for each detector. Further, the number of read circuits required in the entire PET apparatus is several times to several tens of times as much as the read circuits in each detector. This may lead to a concern that the apparatus is significantly increased in size and cost.

In order to solve the above-described problem, NPL 1 proposes an approach using a multiplexer circuit, in which output signals from a plurality of SiPMs are electrically connected in parallel with one read circuit, and each output signal is subjected to centroid calculation, thereby specifying a gamma ray incident position in a detectable region using a small number of read circuits.

In this case, when an SiPM is used as a light-receiving device, a parasitic capacitance included in the SiPM and an input impedance of a signal processing circuit form a low pass filter, which may deteriorate a high-frequency component of a light-receiving signal. In particular, an increased number of parallel connections of SiPMs leads to more deterioration in high-frequency component of the light-receiving signal, so that rising of the light-receiving signal is difficult to be detected. This may deteriorate the property of detecting the timing at which a gamma ray is incident (hereinafter also referred to as a "timing property").

The present invention has been made in order to solve the above-described problems. An object of the present invention is to improve the position detection accuracy while suppressing a deterioration in timing property of the detection signal in a radiation detection device used in a nuclear medicine diagnosis apparatus.

Solution to Problem

A radiation detection device according to the present invention is used in a nuclear medicine diagnosis apparatus. The radiation detection device includes a plurality of scintillators, a semiconductor light-receiving device, a position detection circuit, and a timing detection circuit. Each of the scintillators converts a gamma ray emitted from a subject into fluorescence. The semiconductor light-receiving device is provided corresponding to each of the scintillators, and converts the fluorescence converted by a corresponding one of the scintillators into an electrical signal. Based on the electrical signal from an anode of the semiconductor light-receiving device, the position detection circuit specifies a gamma ray detection position in the scintillators. The timing detection circuit is connected to the anode of the semiconductor light-receiving device and specifies time information corresponding to a time of occurrence of an event in which the gamma ray is detected.

In this way, the receiving position and the detection timing of the gamma ray can be specified using the same electrical signal from the anode of the semiconductor light-receiving device. Thus, by adjusting the electrical signal from the anode, the properties of both position detection and time detection can be changed in the same tendency. Accordingly, the position detection accuracy and the time detection accuracy both can be improved.

Preferably, the scintillators are disposed in a pattern of an array. The position detection circuit specifies a gamma ray detection position in the array based on: a first weighting addition signal of electrical signals in rows of the array; and a second weighting addition signal of electrical signals in columns of the array.

In this way, the detection position of the gamma ray can be specified based on the signal arranged in rows and the signal arranged in columns of the plurality of scintillators that are disposed in a pattern of an array. Thus, in the position detection circuit, the number of signals used for position detection can be smaller than the number of scintillators (that is, the number of semiconductor light-receiving devices). Thereby, increase in size and cost of the apparatus can be suppressed.

Preferably, the radiation detection device further includes: a voltage source; and a centroid calculation circuit that generates the first weighting addition signal and the second weighting addition signal. A plurality of the semiconductor light-receiving devices are connected in parallel between the voltage source and the centroid calculation circuit. Each of the semiconductor light-receiving devices has a cathode connected to the voltage source, and the anode connected to the centroid calculation circuit. When a signal from one of the semiconductor light-receiving devices is detected, the timing detection circuit specifies the time information corresponding to the time of occurrence of an event in which the gamma ray is detected.

By the configuration as described above, when a gamma ray is applied to one of the plurality of semiconductor light-receiving devices connected in parallel, the gamma ray can be appropriately detected by the timing detection circuit.

Preferably, a capacitor is further included, that is connected between the timing detection circuit and the anode of each of the semiconductor light-receiving devices.

As the timing detection circuit is connected to the anode of the semiconductor light-receiving device through the capacitor in this way, the timing detection circuit can detect a high-frequency component (that is, a component with high response speed) of the electrical signal from the semiconductor light-receiving device. Thus, the time detection accuracy for the gamma ray can be improved.

Preferably, the capacitor has a capacitance that is determined in accordance with the number of the semiconductor light-receiving devices connected in parallel with the centroid calculation circuit.

When the semiconductor light-receiving devices are connected in parallel, their parasitic capacitance components and a capacitor that is connected to the timing detection circuit form a low pass filter. The low pass filter may in turn attenuate the high-frequency component of the electrical signal detected in the timing detection circuit, which may lead to a deterioration in the time detection accuracy. Thus, by appropriately setting the capacitance of the capacitor connected to the timing detection circuit in accordance with the number of the semiconductor light-receiving devices connected in parallel, deterioration in time detection accuracy can be suppressed.

Preferably, the number of the semiconductor light-receiving devices connected in parallel with the centroid calculation circuit is determined in accordance with detection accuracy required for the timing detection circuit.

When the semiconductor light-receiving devices are connected in parallel as described above, their parasitic capacitance components form a low pass filter, which influences the time detection accuracy in the timing detection circuit. Thus, by determining the number of semiconductor light-receiving devices connected in parallel in accordance with the detection accuracy required for the timing detection circuit, desired time detection accuracy can be ensured.

A nuclear medicine diagnosis apparatus according to the present invention includes the radiation detection device described in any one of the above.

Advantageous Effects of Invention

According to the present invention, in a radiation detection device used in a nuclear medicine diagnosis apparatus, deterioration in timing property of a detection signal can be suppressed while the position detection accuracy can be improved.

DESCRIPTION OF EMBODIMENTS

Figure 1:
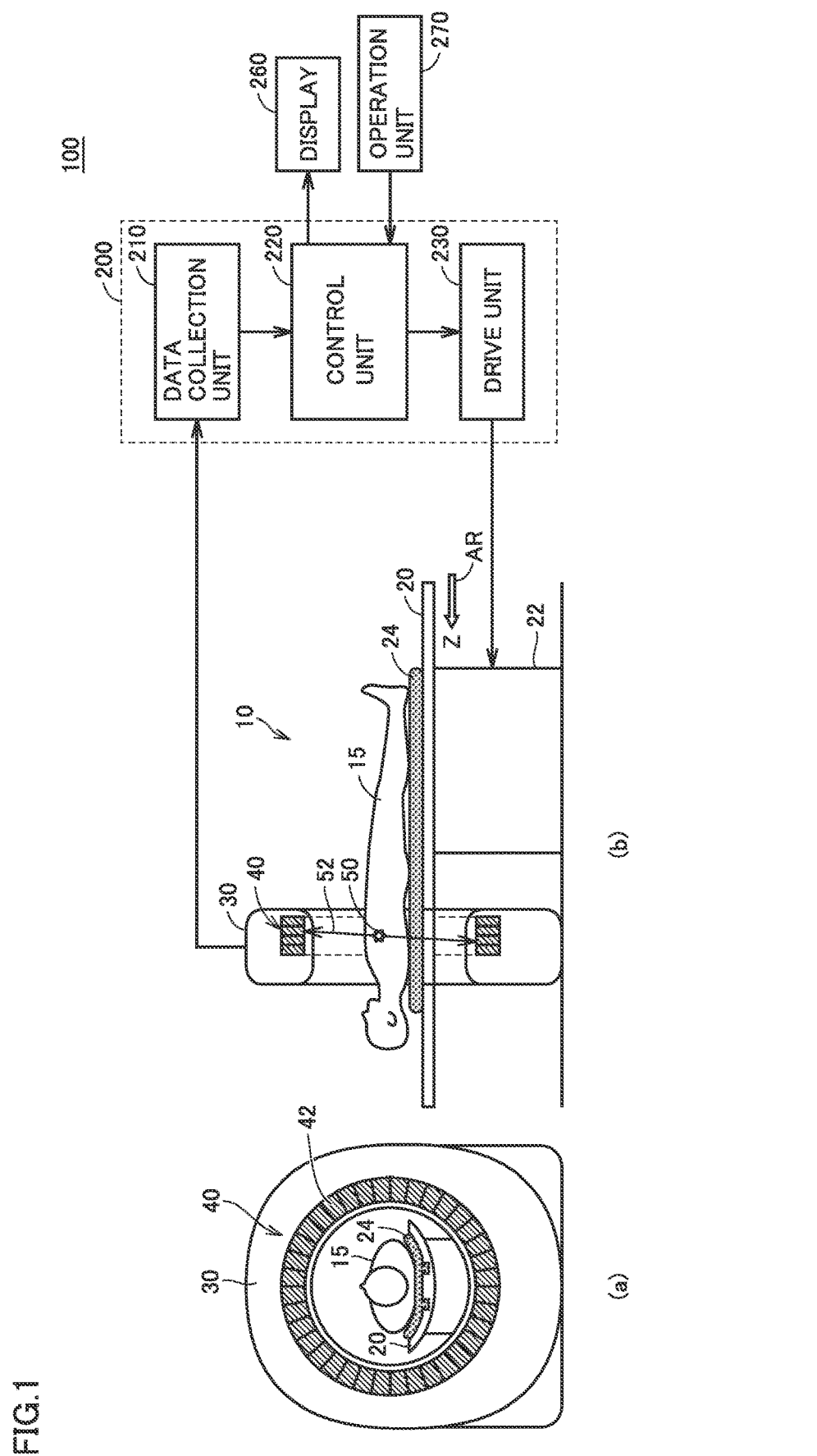
FIG. 1 is an overall schematic diagram of a PET apparatus according to the present embodiment.

The embodiments of the present invention will be hereinafter described in detail with reference to the accompanying drawings, in which the same or corresponding components will be designated by the same reference characters, and the description thereof will not be repeated.

[Configuration of Nuclear Medicine Diagnosis Apparatus]

FIG. 1 is an overall schematic diagram of a nuclear medicine diagnosis apparatus according to the present embodiment. FIG. 1 shows an example in the case where a nuclear medicine diagnosis apparatus is a PET apparatus 100, but the nuclear medicine diagnosis apparatus is not limited thereto, and may be other apparatuses such as an SPECT apparatus, for example, as long as it includes a so-called radiation detector. The present embodiment will be described with reference to an example in which a gamma ray is used as radiation.

Referring to FIG. 1, PET apparatus 100 includes a mount unit 10, a controller 200, a display 260, and an operation unit 270. FIG. 1(a) is a front view of mount unit 10 while FIG. 1(b) is a side view of mount unit 10.

Mount unit 10 includes: a top plate 20 on which a subject 15 is placed; a moving device 22 for moving top plate 20; a gantry 30 formed in an approximately cylindrical shape and having an opening; and a detector ring 40 disposed inside gantry 30.

Controller 200 includes a data collection unit 210, a control unit 220, and a drive unit 230. Control unit 220 is configured, for example, to include a central processing unit (CPU) and a storage device such as a memory. Furthermore, data collection unit 210 and drive unit 230 each may be formed of a microprocessor or a field programmable gate array (FPGA), or may be formed as a part of the CPU in control unit 220.

Subject 15 is placed on a cushion 24 provided on top plate 20. Top plate 20 is provided so as to be moved through openings of gantry 30 and detector ring 40 in the Z direction indicated by an arrow AR in the figure. Top plate 20 can reciprocate in the Z direction. Moving device 22 is controlled by a drive signal from drive unit 230 to adjust the height of top plate 20 and to move top plate 20 in the Z direction, thereby intorducing subject 15 placed on top plate 20 into the opening of gantry 30.

Detector ring 40 is formed by arranging a plurality of unit rings in the Z direction. Each of the plurality of unit rings is formed by a plurality of radiation detectors 42 arranged radially on a flat plane perpendicular to the Z direction.

Figure 2:
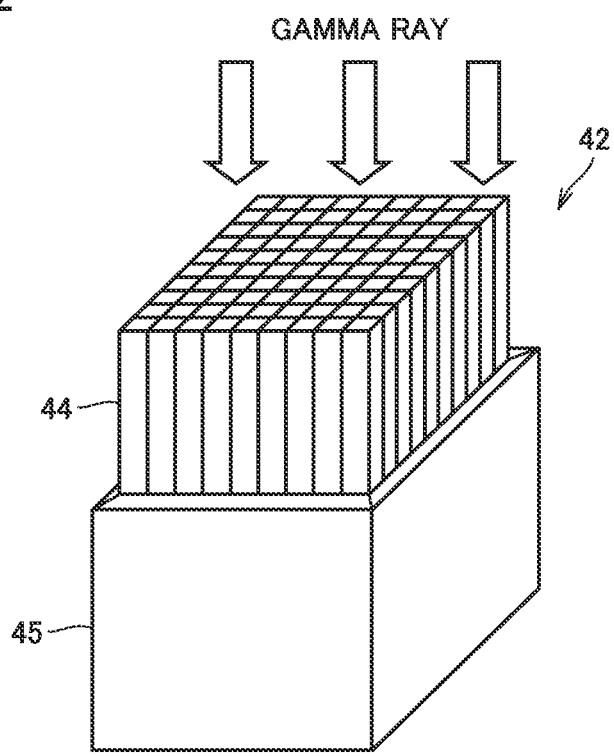
FIG. 2 is a schematic perspective view of a gamma ray detector in FIG. 1.

As shown in FIG. 2, each of radiation detectors 42 (hereinafter also referred to as a "gamma ray detector 42") is configured to include: a scintillator block 44 formed of a plurality of scintillators arranged in a pattern of an array; and a light-receiving sensor 45. Each of the scintillators in scintillator block 44 converts radiation (gamma ray) 52, which is emitted from a radioactive medicine (radioactive tracer) 50 (for example, fluorodeoxyglucose (FDG)) containing a positron-emitting radionuclide administered to subject 15, into fluorescence having a peak in an ultraviolet range. Light-receiving sensor 45 is provided with light-receiving devices corresponding to the respective scintillators. Each of these light-receiving devices multiplies the photoelectron converted by the corresponding scintillator, and converts the multiplied photoelectron into an electrical signal. In the present embodiment, as a light-receiving device, a silicon photomultiplier (SiPM) formed of an avalanche photodiode (AMD) as a semiconductor array is used. Gamma ray detector 42 outputs the generated electrical signal to data collection unit 210 in controller 200 in FIG. 1.

Data collection unit 210 processes the signal received from gamma ray detector 42, and outputs the processed signal to control unit 220. Based on the signal received from data collection unit 210, control unit 220 images the dose distribution of the detected gamma ray and causes display 260 to display the image.

Operation unit 270 is configured to include a pointing device such as a keyboard, a touch panel, and a mouse (each of which is not shown), for example. From an operator, operation unit 270 receives an instruction for operating moving device 22 of mount unit 10, and an instruction for starting/stopping imaging. Operation unit 270 outputs the signal corresponding to the operator's operation to control unit 220. According to the signal from operation unit 270, control unit 220 controls drive unit 230 to drive moving device 22.

In the present embodiment, the configuration including gamma ray detector 42 and data collection unit 210 will be referred to as a "radiation detection device".

Figure 3:
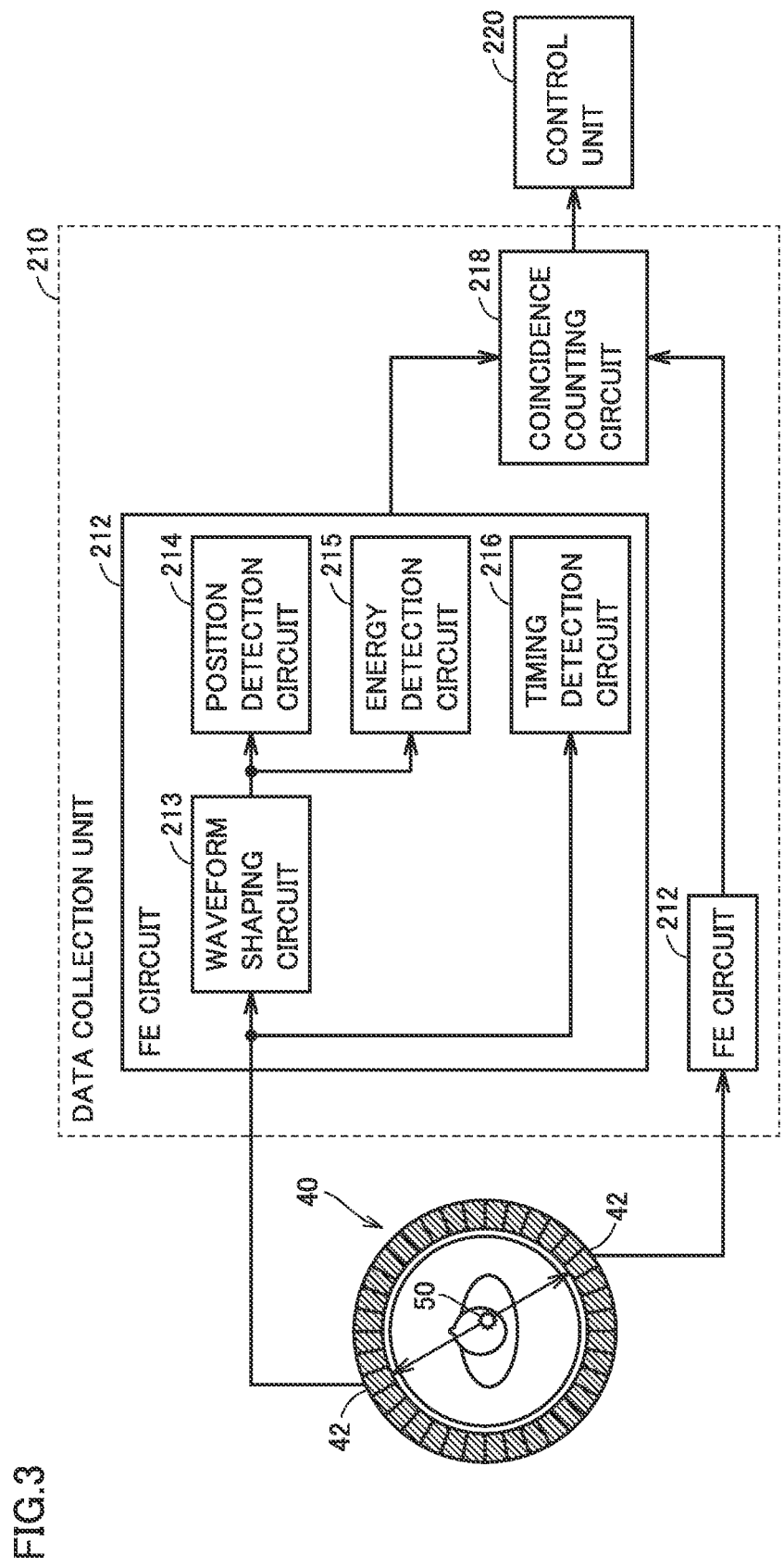
FIG. 3 is a functional block diagram showing details of a data collection unit in FIG. 1.

FIG. 3 is a functional block diagram showing details of data collection unit 210 in FIG. 1. Referring to FIG. 3, data collection unit 210 includes: a front end (FE) circuit 212 provided corresponding to each of gamma ray detectors 42 that constitute detector ring 40; and a coincidence counting circuit 218. Each FE circuit 212 includes a waveform shaping circuit 213, a position detection circuit 214, an energy detection circuit 215, and a timing detection circuit 216.

Waveform shaping circuit 213 receives an electrical signal generated in gamma ray detector 42 and subjects the analog waveform data of this electrical signal to waveform shaping processing. Specifically, waveform shaping circuit 213 subjects the analog waveform data from gamma ray detector 42 as shown in FIG. 4(a) to calculation processing such as integration processing and differentiation processing, and generates data having a peak value exhibiting energy as shown in FIG. 4(b). Waveform shaping circuit 213 outputs the generated data to position detection circuit 214 and energy detection circuit 215.

Position detection circuit 214 receives the data generated in waveform shaping circuit 213, and determines in which scintillator of scintillator block 44 the gamma ray has been detected. Specifically, the centroid position of the data generated in waveform shaping circuit 213 is calculated, thereby specifying the position of the scintillator in which the gamma ray has been detected. Position detection circuit 214 outputs the data showing the specified scintillator position to coincidence counting circuit 218.

Energy detection circuit 215 receives the data generated in waveform shaping circuit 213, and detects energy. Energy detection circuit 215 outputs the data showing the detected energy to coincidence counting circuit 218.

Based on the analog waveform data from gamma ray detector 42 shown in FIG. 4(a), timing detection circuit 216 detects the time information corresponding to the time of occurrence of an event in which the gamma ray is detected, that is, the gamma ray detection time (incident timing). For example, the point of time at which the value of the analog waveform data shown in FIG. 4(a) exceeds a prescribed threshold value is specified as gamma ray detection time. Timing detection circuit 216 outputs the data of the specified detection time to coincidence counting circuit 218.

Coincidence counting circuit 218 receives data from each FE circuit 212, and generates coincidence counting information used for determining the direction in which the pair annihilation gamma ray emitted from a positron is incident. Specifically, based on the data from the plurality of FE circuits 212, coincidence counting circuit 218 searches for a combination of gamma ray detectors in which the gamma ray incident timing (detection time) is within a prescribed time window width and in which the energy of the light receiving signal is within a prescribed energy window width. Then, coincidence counting circuit 218 specifies the combination of gamma ray detectors obtained after the search as gamma ray detectors that have simultaneously detected two annihilation photons emitted from one positron. This means that a radioactive tracer 50 that emits a gamma ray exists on a straight line that connects two specified gamma ray detectors.

Furthermore, based on the data from timing detection circuit 216, coincidence counting circuit 218 calculates the difference in detection time between two annihilation photons emitted from radioactive tracer 50 (that is, a distance from the gamma ray detector to the radioactive tracer: TOF), and specifies the position of radioactive tracer 50 on the straight line that connects the above-mentioned two gamma ray detectors. Coincidence counting circuit 218 outputs the data about the specified position of the gamma ray detector and the specified position of radioactive tracer 50 to control unit 220.

In control unit 220, the data received from coincidence counting circuit 218 is formed again to thereby generate an image of subject 15. Then, this image is displayed on display 260. A diagnostician such as a doctor performs a nuclear medicine diagnosis using the displayed image of subject 15.

The PET apparatus having the above-described configuration requires an image with a higher resolution in order to allow an accurate diagnosis. In order to improve the resolution, it is necessary to (1) improve the accuracy of detecting the gamma ray incident position in each gamma ray detector, and (2) improve the detection accuracy for the gamma ray detection time difference in two gamma ray detectors (time resolution).

For improving the accuracy of detecting the incident position in each gamma ray detector, it is preferable to provide an individual signal processing circuit in each light-receiving device (SiPM) in a one-to-one relation. However, when a large number of light-receiving devices are disposed in a two-dimensional array pattern in one gamma ray detector, the same number of signal processing circuits as that of the light-receiving devices is required. As a result, the entire PET apparatus may require tens of thousands to hundreds of thousands of signal processing circuits. Thereby, the apparatus is increased in size and cost.

There is a configuration proposed for addressing the above-described situation, in which each gamma ray detector employs a multiplexer circuit. In such a configuration, a plurality of light-receiving devices are connected in parallel, and one signal processing circuit is provided for the plurality of light-receiving devices, thereby reducing the number of signal processing circuits in the entire apparatus.

Figure 5:
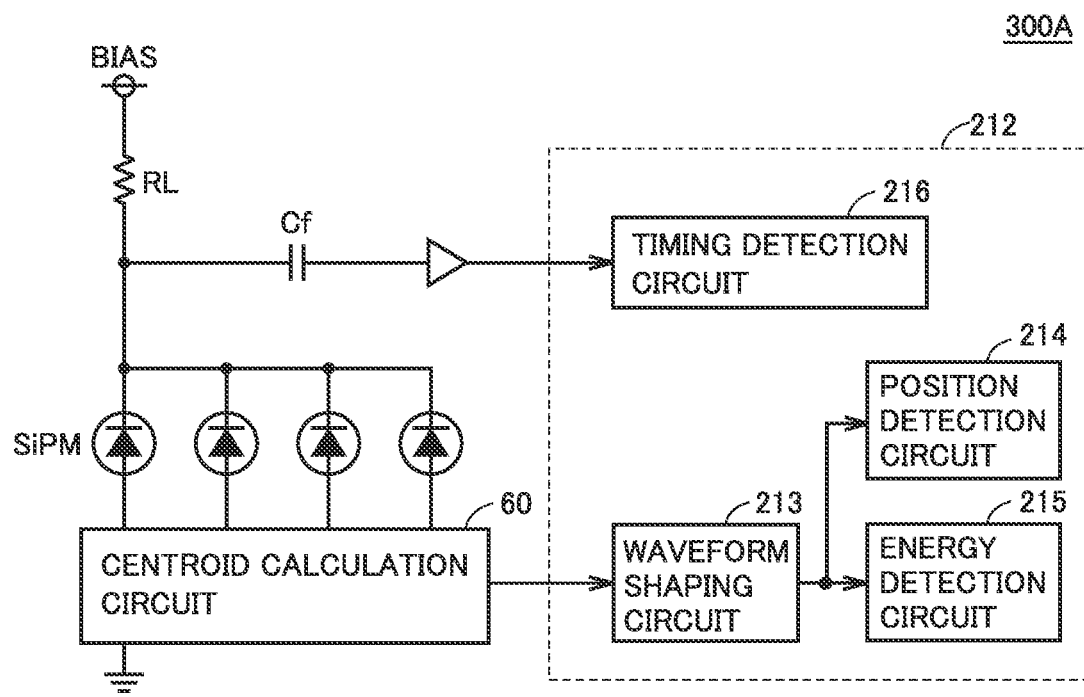
FIG. 5 is a diagram for illustrating a signal processing circuit in a comparative example.

FIG. 5 is a diagram for illustrating a signal processing circuit in a radiation detection device 300A in a comparative example. Referring to FIG. 5, the signal processing circuit in the comparative example includes a bias voltage BIAS, a resistance RL, a plurality of SiPMs as light-receiving devices, a centroid calculation circuit 60, and a capacitor Cf.

Figure 6:
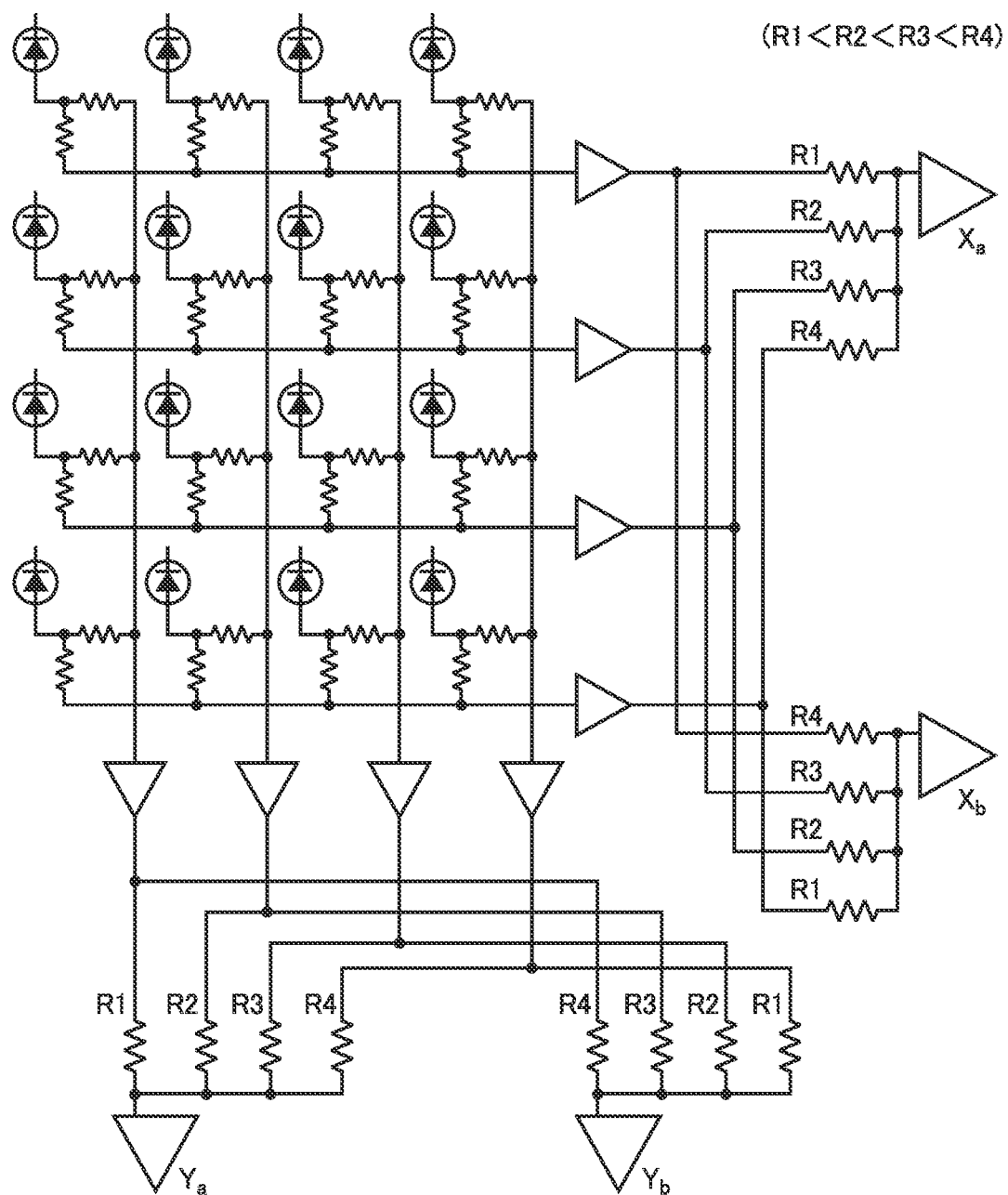
FIG. 6 is a diagram for illustrating an example of the configuration of a centroid calculation circuit.

The plurality of SiPMs are provided corresponding to the plurality of scintillators (FIG. 2) disposed in the array pattern. Also, the plurality of SiPMs are arranged in the array pattern as shown in FIG. 6. FIG. 6 shows an example in which sixteen SiPMs are disposed as a 4×4 array.

Resistance RL has one end connected to bias voltage BIAS and the other end connected to a cathode of each of the plurality of the SiPMs. The SiPMs have anodes each connected to centroid calculation circuit 60.

Furthermore, one end of resistance RL (the cathode of the SiPM) is connected also to timing detection circuit 216 of FE circuit 212 through capacitor Cf. Through capacitor Cf, only the high-frequency component in the voltage fluctuation in the anode (that is, a node ND) of the SiPM is transmitted to timing detection circuit 216.

Figure 4:
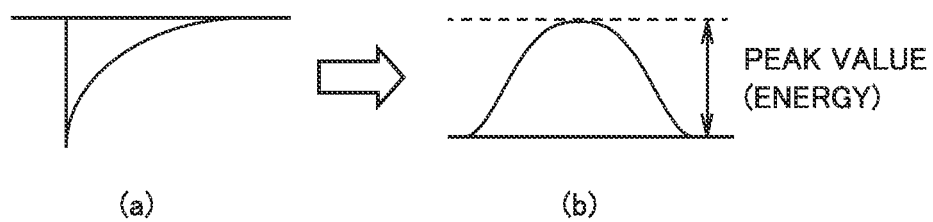
FIG. 4 is a diagram for illustrating a waveform shaping circuit in FIG. 3.

When a gamma ray is incident upon gamma ray detector 42 and detected by one of the plurality of SiPMs, a current flows through the SiPM in which the gamma ray has been detected, with the result that the voltage on node ND decreases in an impulse pattern as shown in FIG. 4(*a*). When the decreased amount of this voltage is larger than a prescribed amount, a signal is output to timing detection circuit 216. Thereby, timing detection circuit 216 specifies the time at which the gamma ray has been detected.

Centroid calculation circuit 60 serves to generate a signal for determining, from among the plurality of SiPMs disposed in the pattern of an array, a specific SiPM in which a gamma ray has been detected. Specifically, as shown in FIG. 6, each of the parallel signals in rows of the SiPMs arranged in the array pattern is weighted and added by a corresponding one of resistances R1 to R4, thereby generating position detection signals Xa and Xb. Similarly, each of the parallel signals in columns of the SiPMs is weighted and added by a corresponding one of resistances R1 to R4, thereby generating position detection signals Ya and Yb. The generated position detection signals are output to waveform shaping circuit 213 in FE circuit 212.

For example, in the case where the resistance values are set on the condition that R1<R2<R3<R4, position detection signal Xa exhibits an amplitude that is maximized when the gamma ray is detected in the SiPM on the first row, and exhibits an amplitude that is minimized when the gamma ray is detected in the SiPM on the fourth row. In other words, based on the amplitude of position detection signal Xa, it can be specified in which row's SiPM the gamma ray has been detected. Similarly, based on the amplitude of position detection signal Ya, it can be specified in which column's SiPM the gamma ray has been detected. Accordingly, by using position detection signals Xa and Ya, an SiPM in which the gamma ray has been detected can be specified from among the SiPMs arranged in an array pattern (position detection circuit 214).

In addition, for position detection signal Xb, the resistances in respective rows are connected in reverse order to the resistances in respective rows for position detection signal Xa. Also, for position detection signal Yb, the resistances in respective columns are connected in reverse order to the resistances in respective columns for position detection signal Ya. Thus, position detection signals Xb and Yb are opposite in order of amplitude level to position detection signals Xa and Ya, respectively. For example, position detection signal Xb exhibits an amplitude that is minimized when a gamma ray is detected in the SiPM on the first row, and exhibits an amplitude that is maximized when a gamma ray is detected in the SiPM on the fourth row. By using the position detection signals having opposite tendencies in this way, the SiPM in which a gamma ray has been detected can be specified correctly, for example, even in the case where an offset occurs in the entire signals.

In the signal processing circuit in the comparative example shown in FIG. 5, the voltage fluctuation on node ND needs to be increased in order to improve the accuracy of the gamma ray detection time. Accordingly, resistance RL connected to bias voltage BIAS needs to be increased. In this case, however, it takes time to charge capacitor Cf after detection of the gamma ray by the SiPM is ended. This slows the response of the position detection signal in centroid calculation circuit 60. Thereby, the position detection accuracy may deteriorate.

On the other hand, when resistance RL is reduced in order to improve the position detection accuracy, the amount of voltage drop on node ND is reduced to the contrary, which deteriorates the accuracy of the gamma ray detection time (time resolution). In other words, in the signal processing circuit shown in FIG. 5, a trade-off relation is established between the position detection accuracy and the time resolution, which leads to difficulty in improving the detection accuracy for both position and time.

Figure 7:
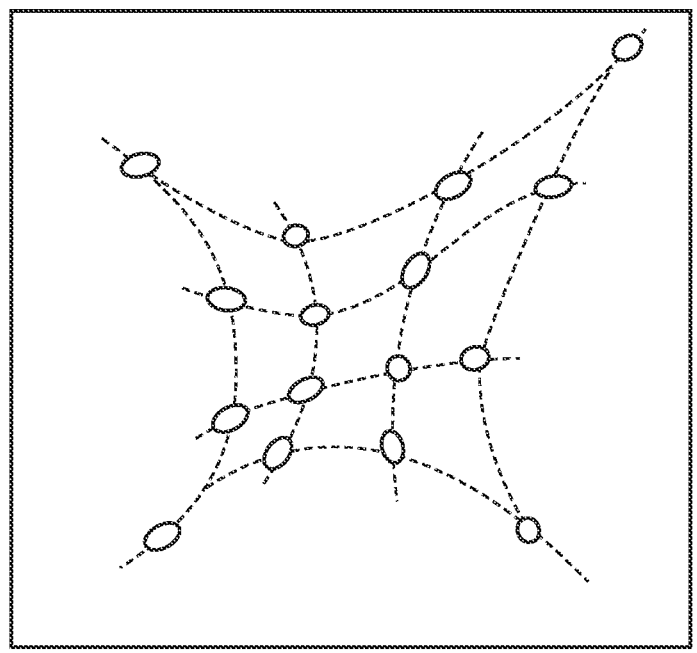
FIG. 7 is a diagram showing an example of a position detection map detected in the comparative example.
Figure 8:
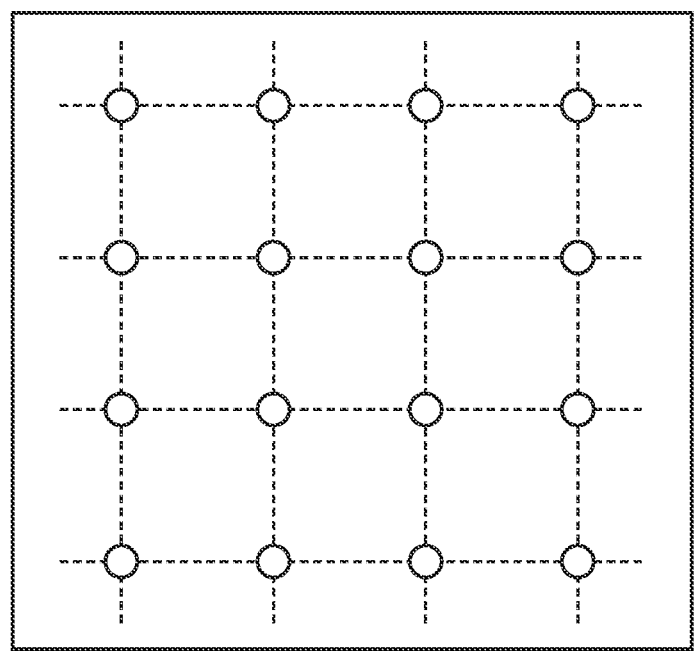
FIG. 8 is a diagram showing an ideal position detection map.

FIG. 7 shows an example of a gamma ray position detection map by an array of 4×4 SiPMs in the case where signal processing in this comparative example is used. FIG. 7 shows a map in which sixteen SiPMs are distinguishable, but this map is largely distorted as compared with the ideal position detection map as shown in FIG. 8.

Figure 9:
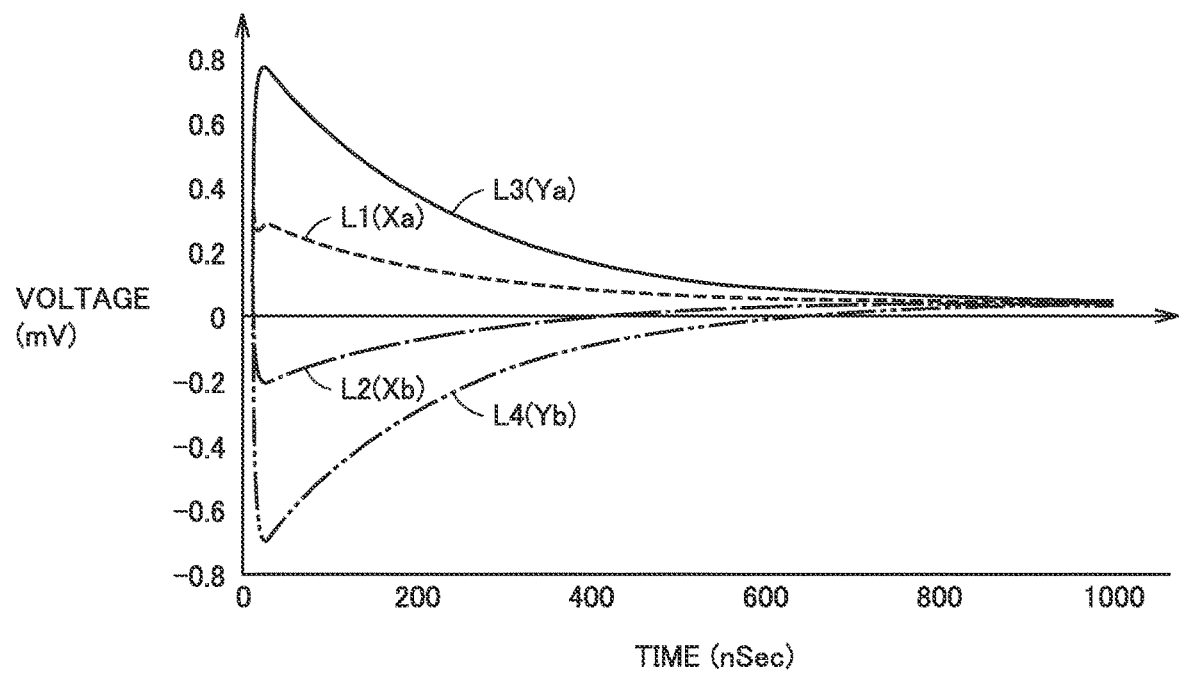
FIG. 9 is a diagram showing an example of a centroid calculation waveform in the comparative example.

Furthermore, FIG. 9 shows examples of position detection signals Xa, Xb, Ya, and Yb output from centroid calculation circuit 60 in a comparative example. As apparent from FIG. 9, in the case where a signal processing circuit in the comparative example is used, some of the position detection signals (L2 (Xb) and L4 (Yb) in FIG. 9) exhibit an amplitude of the negative voltage value. Thus, the detection position in position detection circuit 214 cannot be correctly specified.

In order to solve the above-described problems, the present embodiment employs a configuration in which the timing signal for specifying the gamma ray detection time is read from the anode side in each SiPM and resistance RL in the signal processing circuit in FIG. 5 is not used. This configuration can prevent a decrease in responsiveness of the position detection signal resulting from resistance RL, and also can prevent a level decrease in timing signal, so that both the position detection accuracy and the time resolution can be improved.

Figure 10:
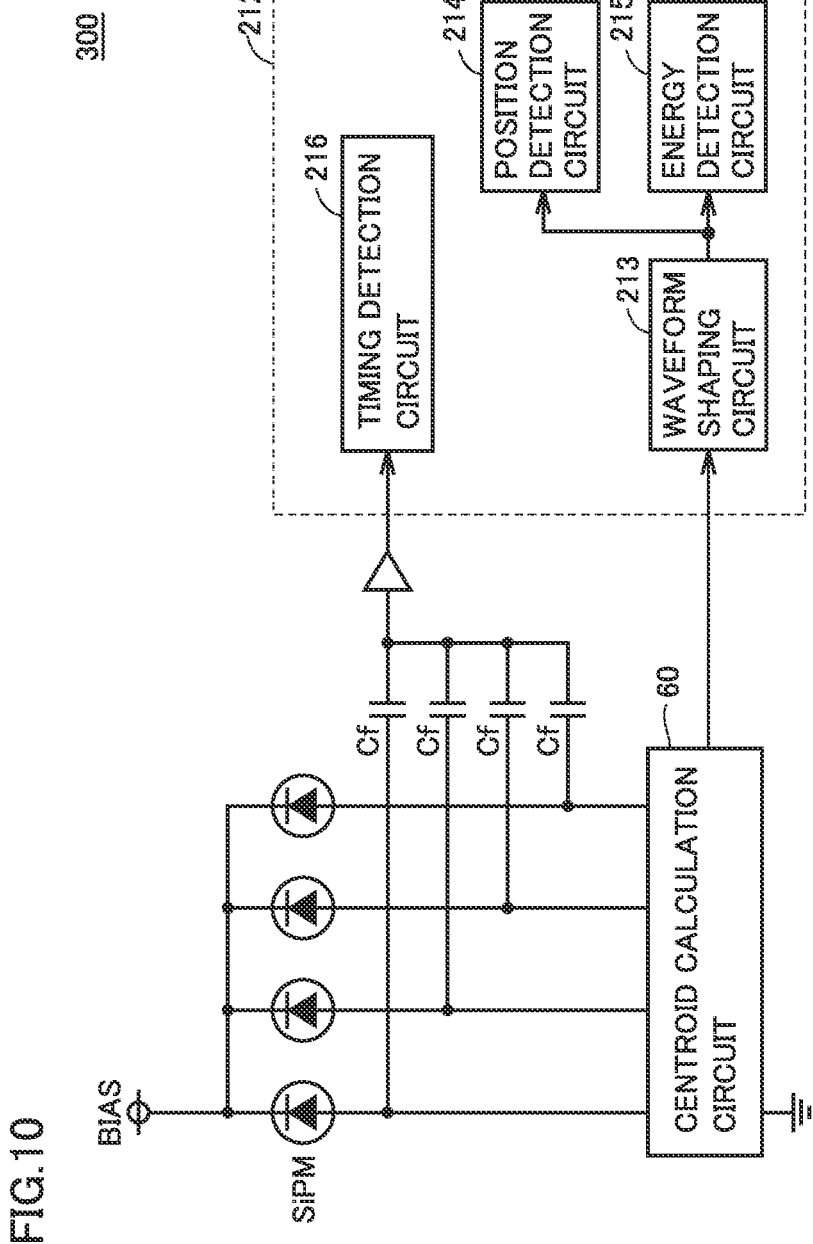
FIG. 10 is a diagram for illustrating a signal processing circuit in the present embodiment.

FIG. 10 is a diagram for illustrating a signal processing circuit in a radiation detection device 300 according to the present embodiment. Referring to FIG. 10, in the signal processing circuit, a plurality of SiPMs have: cathodes each connected to a bias voltage BIAS not through a resistance; and anodes each connected to centroid calculation circuit 60. Furthermore, the anodes of the SiPMs are connected in parallel through respective capacitors Cf and further connected to timing detection circuit 216 of FE circuit 212.

In this way, there is no resistance component (bias resistance) connected to bias voltage BIAS, so that a decrease in responsiveness of the position detection signal in centroid calculation circuit 60 can be suppressed. Furthermore, since a timing signal is obtained from the anode side of the SiPM, the difference between the voltage upon detection of a gamma ray and the voltage upon detection of no gamma ray can be sufficiently ensured even without a bias resistance. Thereby, a level decrease in the timing signal can be suppressed. Therefore, the position detection accuracy and the detection time accuracy (time resolution) can be improved.

In this case, when the impedance in the read circuit (FE circuit 212) for the timing signal is increased by the parasitic capacitance component in the SiPM, a low pass filter is formed. Accordingly, the high-frequency component of the timing signal may be cut to thereby deteriorate the signal. Thus, it is desirable that the detection circuit for the timing signal is configured to exhibit a lowest possible input impedance.

Also, it is preferable to determine the capacitance of capacitor Cf in accordance with the parasitic capacitance component of the SiPM. In other words, it is desirable to determine the capacitance of capacitor Cf in accordance with the number of SiPMs that are connected in parallel in the centroid calculation circuit.

Alternatively, with respect to the prescribed capacitance of capacitor Cf, the number of SiPMs connected in parallel may be determined in accordance with the deterioration state of the timing signal to be permitted (that is, the detection accuracy required for the timing detection circuit).

Figure 11:
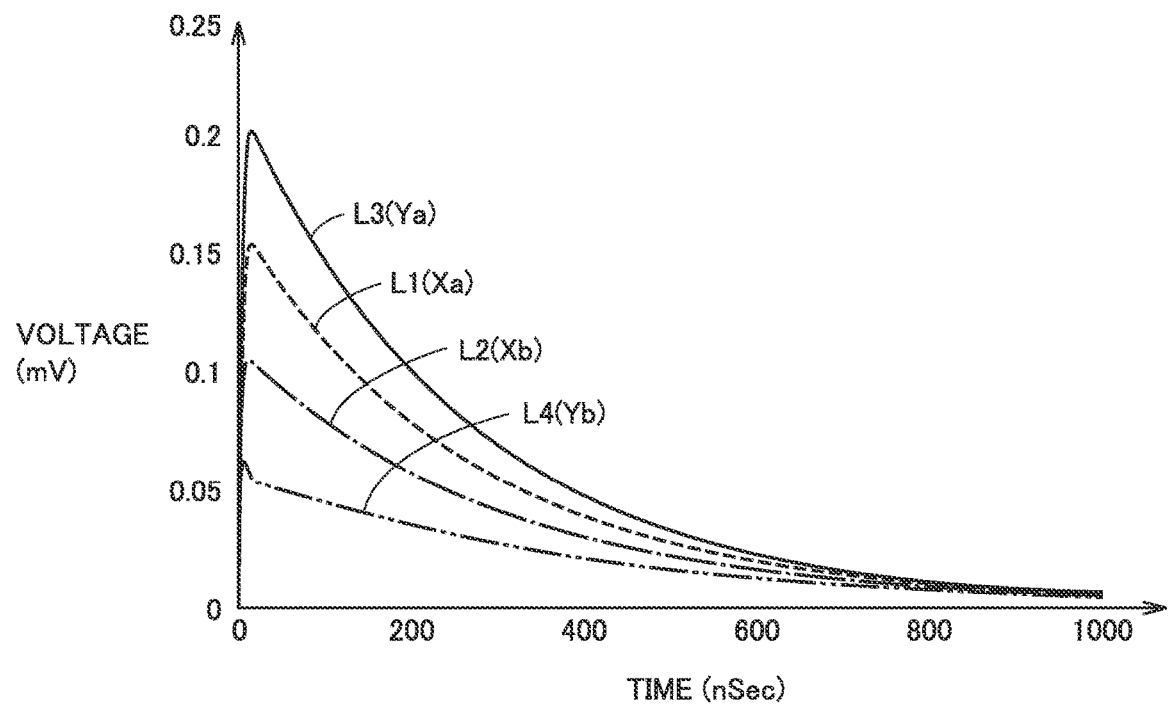
FIG. 11 is a diagram showing an example of a centroid calculation waveform in the present embodiment.

FIG. 11 shows examples of position detection signals Xa, Xb, Ya, and Yb output from centroid calculation circuit 60 in the case where the radiation detection device according to the present embodiment is used. In FIG. 11, each of position detection signals Xa, Xb, Ya, and Yb exhibits an amplitude having a positive voltage value in contrast to FIG. 9 in the comparative example. Accordingly, by using the signal processing circuit in the present embodiment, the distortion of the position detection map as shown in FIG. 7 in the comparative example can be reduced.

Figure 12:
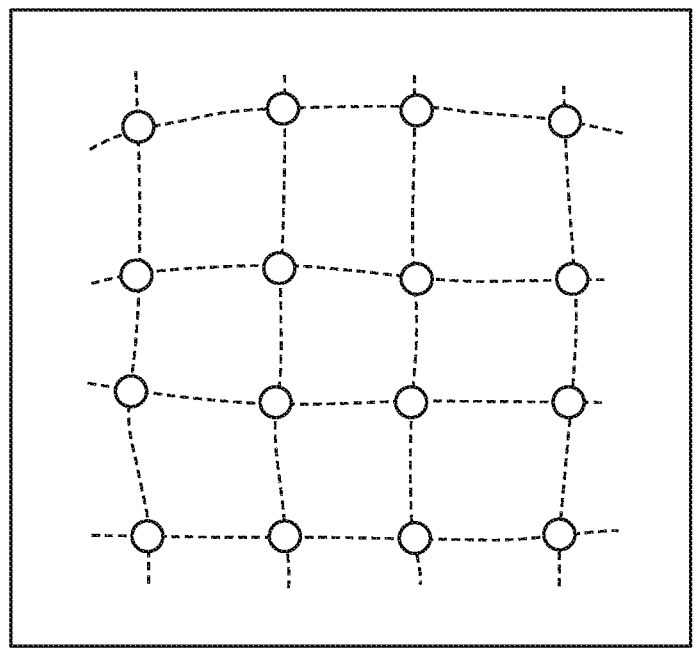
FIG. 12 is a diagram showing an example of a position detection map in the present embodiment.

FIG. 12 is a diagram showing an example of a gamma ray position detection map by an array of 4×4 SiPMs in the case where the radiation detection device according to the present embodiment is used. The position detection map in FIG. 12 is reduced in distortion as compared with the position detection map in FIG. 7 shown in the comparative example. Thus, the position detection map in FIG. 12 is closer to the ideal position detection map shown in FIG. 8. As apparent from FIG. 12, in the case where the radiation detection device according to the present embodiment is used, the positional relation among the SiPMs arranged in a lattice pattern can be correctly recognized.

Figure 13:
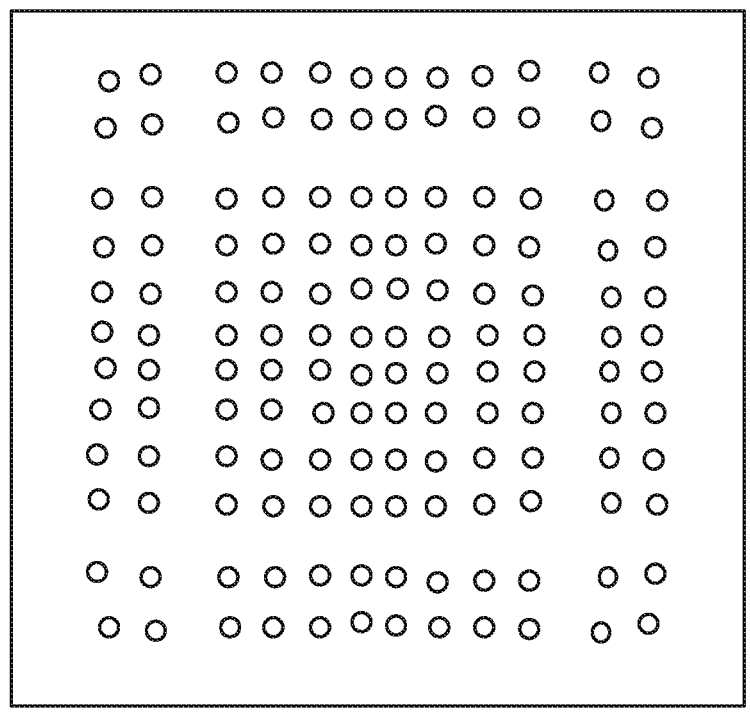
FIG. 13 is a diagram showing another example of the position detection map in the present embodiment.

Furthermore, FIG. 13 shows an example of the position detection map obtained in the case where the number of SiPMs is further increased. In FIG. 13, a total of 144 (12×12) SiPMs are used. Also in FIG. 13, the positions of SiPMs arranged in a lattice pattern can be entirely correctly grasped though there is a slight distortion.

By using the radiation detection device according to the present embodiment as described above, the position detection accuracy and the time resolution for the radiation emitted from a subject can be improved in a nuclear medicine diagnosis apparatus.

It should be understood that the embodiments disclosed herein are illustrative and non-restrictive in every respect. The scope of the present invention is defined by the terms of the claims, rather than the description above, and is intended to include any modifications within the meaning and scope equivalent to the terms of the claims.

REFERENCE SIGNS LIST 10 mount unit, 15 subject, 20 top plate, 22 moving device, 24 cushion, 30 gantry, 40 detector ring, 42 gamma ray detector, 44 scintillator block, 45 light-receiving sensor, 50 radioactive tracer, 60 centroid calculation circuit, 100 PET apparatus, 200 controller, 210 data collection unit, 212 FE circuit, 213 waveform shaping circuit, 214 position detection circuit, 215 energy detection circuit, 216 timing detection circuit, 218 coincidence counting circuit, 220 control unit, 230 drive unit, 260 display, 270 operation unit, 300, 300A radiation detection device, BIAS bias voltage, Cf capacitor, ND node.

The invention claimed is:

1. A radiation detection device used in a nuclear medicine diagnosis apparatus, the radiation detection device comprising:
- a plurality of scintillators, each of which converts a gamma ray emitted from a subject into fluorescence and are disposed in a pattern of an array;
- a semiconductor light-receiving device that is provided corresponding to each of the scintillators, and converts the fluorescence converted by a corresponding one of the scintillators into an electrical signal;
- a position detection circuit that specifies a gamma ray detection position in the scintillators based on the electrical signal from an anode of the semiconductor light-receiving device; and
- a timing detection circuit that is connected to the anode of the semiconductor light-receiving device and specifies time information corresponding to a time of occurrence of an event in which the gamma ray is detected,
- wherein the position detection circuit specifies a gamma ray detection position in the array based on a first weighting addition signal of electrical signals in rows of the array and a second weighting addition signal of electrical signals in columns of the array, and
- wherein the radiation detection deice further comprises:
  - a power supply,
  - a centroid calculation circuit that generates the first weighting additional signal and the second weighting addition signal; and
  - a capacitor that is connected between the timing detection circuit and the anode of each of the semiconductor light-receiving devices,
    - wherein the capacitor has a capacitance in accordance with a number of the semiconductor light-receiving deices connected in parallel with the centroid calculation circuit.

2. The radiation detection device according to claim 1, wherein a plurality of the semiconductor light-receiving devices are connected in parallel between the power supply and the centroid calculation circuit,
wherein each of the semiconductor light-receiving devices has a cathode connected to the power supply, and the anode connected to the centroid calculation circuit, and
wherein when a signal from one of the semiconductor light-receiving devices is detected, the timing detection circuit specifies the time information.

3. The radiation detection device according to claim 2, wherein a number of the semiconductor light-receiving devices connected in parallel with the centroid calculation circuit is a number depending on detection accuracy required for the timing detection circuit.

4. A nuclear medicine diagnosis apparatus comprising the radiation detection device according to claim 1.

5. A radiation detection device used in a nuclear medicine diagnosis apparatus, the radiation detection device comprising:
- a plurality of scintillators, each of which converts a gamma ray emitted from a subject into fluorescence and are disposed in a pattern of an array;
- a semiconductor light-receiving device that is provided corresponding to each of the scintillators, and converts the fluorescence converted by a corresponding one of the scintillators into an electrical signal;
- a position detection circuit that specifies a gamma ray detection position in the scintillators based on the electrical signal from an anode of the semiconductor light-receiving device; and
- a timing detection circuit that is connected to the anode of the semiconductor light-receiving device and specifies time information corresponding to a time of occurrence of an event in which the gamma ray is detected,
- wherein the position detection circuit specifies a gamma ray detection position in the array based on a first weighting addition signal of electrical signals in rows of the array and a second weighting addition signal of electrical signals in columns of the array;
- wherein the radiation detection device further comprises:
  - a power supply; and
  - a centroid calculation circuit that generates the first weighting addition signal and the second weighting addition signal,
- wherein a plurality of the semiconductor light-receiving devices are connected in parallel between the power supply and the centroid calculation circuit,
- wherein each of the semiconductor light-receiving devices has a cathode connected to the power supply, and the anode connected to the centroid calculation circuit,
- wherein when a signal from one of the semiconductor light-receiving devices is detected, the timing detection circuit specifies the time information, and wherein a number of the semiconductor light-receiving devices connected in parallel with the centroid calculation circuit is a number depending on detection accuracy required for the timing detection circuit.

* * * * *